United States Patent [19]

Keith

[11] Patent Number: 4,482,533

[45] Date of Patent: Nov. 13, 1984

[54] POLYMERIC DIFFUSION MATRIX CONTAINING PROPRANOLOL

[75] Inventor: Alec D. Keith, Miami, Fla.

[73] Assignee: Key Pharmaceuticals, Inc., Miami, Fla.

[21] Appl. No.: 479,499

[22] Filed: Mar. 28, 1983

Related U.S. Application Data

[63] Continuation of Ser. No. 338,256, Jan. 11, 1982, abandoned.

[51] Int. Cl.$^3$ .................. A61L 15/03; A61K 9/70; A61F 13/00
[52] U.S. Cl. .................................... 421/28; 424/78
[58] Field of Search ........................ 424/28, 78

[56] References Cited

U.S. PATENT DOCUMENTS

| | | | |
|---|---|---|---|
| 2,155,658 | 4/1939 | Herrmann et al. | 424/78 |
| 2,160,503 | 5/1939 | Herrmann et al. | 424/78 |
| 2,693,438 | 11/1954 | Ward | 424/28 |
| 2,698,822 | 1/1955 | Halporn et al. | 424/78 |
| 2,726,982 | 12/1955 | Ochs | 424/78 |
| 2,830,370 | 4/1958 | Rothrock | 32/2 |
| 3,214,338 | 10/1965 | Ehrlich | 424/78 |
| 3,287,222 | 11/1966 | Larde et al. | 424/28 |
| 3,339,546 | 9/1967 | Chen | 128/156 |
| 3,429,308 | 2/1969 | Russell | 424/14 |
| 3,444,858 | 5/1969 | Russell | 424/28 |
| 3,608,070 | 9/1971 | Nouvel | 424/28 |
| 3,627,871 | 12/1971 | Groves et al. | 424/28 |
| 3,742,951 | 7/1973 | Zaffaroni | 424/28 |
| 3,789,119 | 1/1974 | Fusarl et al. | 424/78 |
| 3,803,300 | 4/1974 | Pospisihil | 424/80 |
| 3,892,905 | 7/1975 | Albort | 252/89 |
| 3,972,995 | 8/1976 | Tsuk et al. | 424/28 |
| 4,059,686 | 11/1977 | Tanaka et al. | 424/19 |
| 4,091,091 | 5/1978 | Terrill | 424/80 |
| 4,210,633 | 7/1980 | Takrurl et al. | 424/28 |
| 4,226,848 | 10/1980 | Nagai et al. | 424/19 |
| 4,291,015 | 9/1981 | Keith et al. | 424/28 |
| 4,292,299 | 9/1981 | Suzuki et al. | 424/16 |
| 4,394,390 | 7/1983 | Hussain et al. | 424/19 |

FOREIGN PATENT DOCUMENTS

| | | |
|---|---|---|
| 0013606 | 7/1980 | European Pat. Off. . |
| 1090184 | 11/1967 | United Kingdom . |
| 1108837 | 4/1968 | United Kingdom . |
| 1343374 | 1/1974 | United Kingdom . |
| 1427881 | 3/1976 | United Kingdom . |
| 2021610A | 12/1979 | United Kingdom . |

OTHER PUBLICATIONS

Fung et al. J. Pharm. Scl. 63110:1810–1811 Nov. 1974.
Chem. Abstr. 94 #180691y #90211n(1981)92 #15196 S(1980)91 #186399 S(1979).
Chem. Abstr. 91#1016ys y(1979).
Chem. Abstr. 94#20412 e(1981)92 #169275D(1980)89#117911b(1978)87#141303J(1977).
Chem. Abstr. 86#161344f(1977)85#10419n(1976)83#120886D#1523-89k(1975).
Chem. Abst. 81#54465w(1974)80#100230v(1974)79#45845B(1973)-75#1330Y3M(1971).
Chem. Abstr. 71#42262N(1969)47#7165 DIF(1953).
Chem. Abstr. 79(8)45845 Aug. 6, 1973, of USSR 219116 Mar. 20, 1973 Uishvevski et al.
Chem. Abstr. 32#8041(9)(1938)38#4343(5)(1944)44#3302e(1950)47#10958 (1953).
Chem. Abstr. 50#652A(1956)52#18889(1958).
Chem. Abstr. 52#10689h(1950)81#684945(1974)85#639285(1976)81-#137100z(1974).
Agosti C.A. 70#27435c(1969).
Bartsct et al. C.A. 73#107928T(1970).
Wagner et al. C.A. 80#22523B (1974).
Kates C.A. 88#163815A (1978).
Henry et al. C.A. 92#15196s(1980).
De Boer et al. (I) 94#131922r(1981).

*Primary Examiner*—Shep K. Rose
*Attorney, Agent, or Firm*—Wegner & Bretschneider

[57] ABSTRACT

A self-supporting polymeric diffusion matrix provides for the sustained release of propranolol in order to deliver said propranolol to a patient. The matrix comprises from about 1 to about 60% by weight of a polar plasticizer, from about 5 to about 20% by weight polyvinylalcohol having a molecular weight from about 50,000 to about 150,000, from about 10 to about 25% by weight polyvinylalcohol having a molecular weight from about 4,000 to about 15,000, from about 2 to about 30% by weight polyvinylpyrrolidone, and a pharmaceutically effective amount of the propanolol to provide a sustained release of said propranolol over a prolonged period.

1 Claim, No Drawings

POLYMERIC DIFFUSION MATRIX CONTAINING PROPRANOLOL

This application is a continuation of Ser. No. 338,256, filed Jan. 11, 1982, now abandoned.

SUMMARY OF THE INVENTION

The present invention relates to a polymeric diffusion matrix containing 1-isopropylamino-3-(1-naphthyloxy)-2-propanol, also known as "propranolol". More particularly, the invention relates to a polymeric diffusion matrix containing propranolol characterized by a sustained release of the propranolol. Propranolol is a widely used beta-adrenergic blocking agent, indicated for the control of hypertension, arrhythmias, and migraine. By the term "propranolol" there is contemplated a mixture of the D and L forms, although the L form is recognized as the preferred therapeutic agent. While the L form may be used alone, for a prolonged sustained release product it is also contemplated that a mixture of the D and L forms could be used. In addition to propranolol itself, "propranolol" includes various pro froms, including the lower aliphatic, araliphatic, and aryl esters, both substituted and unsubstituted forms. As lower aliphatic esters may be mentioned lower alkyl esters; as an aryl ester may be mentioned the benzoic acid ester.

A self-supporting polymeric diffusion matrix is provided for the sustained release of propranolol in order to deliver said propranolol to a patient and provide said patient with the above recited effects, said matrix comprising from about 1 to about 60% by weight of a polar plasticizer; from about 6 to about 30% by weight polyvinylalcohol; from about 2 to about 30% by weight polyvinylpyrrolidone; and a pharmaceutically effective amount of propranolol to provide a sustained release of said propranolol over a prolonged period.

Polar plasticizers suitable for use in this invention include principally poly-loweralkylene oxides, but other polar plasticizers such as diethylphthalic diethylphthalate may be used.

In one embodiment the polar plasticizer is glycerol present in an amount of from about 2 to about 60% by weight. In another embodiment the polar plasticizer is polyethyleneglycol present in an amount of from about 1 to about 15% by weight. A still further embodiment contemplates a mixture of glycerol and polyethyleneglycol wherein the latter is present in an amount by weight of from about 1 to about 5 parts per weight glycerol.

The self-supporting polymeric diffusion matrix generally contains a mixture of polyvinylalcohol and polyvinylpyrrolidone, although it will be understood that other polymeric mixtures may be used provided they yield the desired sustained release effect. For example, both the polyvinylalcohol and the polyvinylpyrrolidone may be partially or completely replaced with from about 1 to about 9% agar or agarose, and preferably from about 1.5 to about 3% agar or agarose, 2% agar or agarose being particularly preferred.

As the polyvinylalcohol used in the present invention, there is generally contemplated one having a molecular weight from about 50,000 to about 150,000, and more preferably about 100,000 to about 150,000, 115,000 having been used in related systems of the present inventors with success. The polyvinylalcohol should be hydrolyzed, generally at least to the extent of 90% with a preferred embodiment being at least 95% hydrolyzed. The polyvinylpyrrolidone should have a molecular weight of from about 15,000 to about 85,000, and more preferably from about 20,000 to about 60,000. Polyvinylpyrrolidone with a molecular weight of 40,000 is a particularly preferred embodiment.

The amount by weight of the ingredients other than the polar plasticizer generally should be in the following ranges: Polyvinylalcohol is generally present in an amount of from about 6 to about 30% by weight, with 20% being a preferred embodiment; polyvinylpyrrolidone is present generally in an amount of from about 2 to about 30% by weight, with about 10% being preferred.

In particular embodiments of this invention the total amount of polyvinylalcohol and polyvinylpyrrolidone used is from about 25% to about 50% by weight.

The water-soluble polymer can be replaced with (in addition to agar) gum arabic, gum tragacanth, polyacrylic acid, polymethacrylic acid, polyvinyloxazolidone, polyvinylmorpholinone, and polyvinylpiperidone.

Polyalkylene glycols (poly-loweralkylene oxides) such as polyethyleneglycol and polypropylene glycol may replace all or part of the glycerol.

In forming the matrix, excess water is not required. In accordance with a preferred aspect of the present invention, about 2% by weight propranolol is included in the diffusion matrix. The resultant homogeneous mixture is poured into forms preferably made of glass or stainless steel. For transdermal application a diffusion matrix with a thickness of about 1 to about 3 mm is in accordance with a preferred aspect of this invention. This diffusion matrix can be cut to obtain the desired surface area once it is suitably cured.

The following methods may be used for preparing the diffusion matrix of the present invention.

In one method, the matrix is formed at atmospheric pressure. Water and polar plasticizer are first mixed together. A polar plasticizer such as glycerol or polyethyleneglycol component is used in the matrix. A matrix formed without a polar plasticizer is not flexible and has poor diffusional contact with the skin, causing unreliable diffusion release. The polyvinylalcohol and polyvinylpyrrolidone are then added to the polar plasticizer water mixture at room temperature with agitation. The mixture is heated to a temperature within the range of from about 90° to about 95° C. at atmospheric pressure to extend the polymers. If desired, the mixture may be maintained at an elevated temperature for a period of time, based on polymer stability, prior to addition of the drug. Thus, the mixture is stable for a period of time and may be kept for such a period before being mixed with the drug to be delivered to the patient. Thereafter, the mixture is temperature-adjusted and the drug to be applied to the patient is then added to the mixture, with thorough agitation. Once a homogeneous mixture of the polymer solution and drug is obtained, the mixture is ready to be cast to form in a drug-containing diffusion matrix. After casting, the mixture is cooled to a temperature such that gelation occurs.

In another method, the polymeric material is heated under pressure to accomplish dissolution in the mixture, the propranolol is mixed in and the material is extruded under pressure into a mold of suitable size and geometry. The use of pressure allows for the incorporation of higher amounts of polymeric material into the matrix, up to 60% total polyvinylpyrrolidone and polyvinylalcohol content, thus improving film strength content, and dimensional stability and allowing for thinner matrices. This pressure method further reduces or eliminates altogether curing and/or drying time.

In a further embodiment there is provided a pH buffer having a sufficiently large molecular structure so that it would not pass through the skin, thus providing a sufficiently high pH to operate in the preferred aspect of the invention, without having base molecules pass through the skin. A pH of at least 7.5 is preferred. This aspect of the invention is accomplished through the provision of Eudraget ® polymers, charged polymers such as poly(methyl methacrylate) and poly(acrylic acid). In one embodiment polymethacrylic acid saturated with choline is used as the polymer, e.g., in an amount of 10% by weight of the total diffusion matrix composition. Thus, for example, such a polymer may be added to the ingredients of Example I below to provide a pH stabilized diffusion matrix to facilitate the diffusion of the propranolol through the skin by maintaining a desirably high enough pH.

It has been further found that curing is facilitated by subjecting the matrix to a temperature down to about −20° C. immediately after casting, especially when polyethyleneglycol is used as the plasticizer. The setting time is quickened considerably.

Sodium dodecyl sulfate or sorbitan (Tween-20) or other detergents may be added in an amount of 0.1 to 10% by weight, based on the matrix, as a dispersing agent, if desired. Up to 10% of one or more absorption facilitators to insure skin penetration such as dimethylsulfoxide, decylmethylsulffoxime, or other penetration enhancers may also be added. Suitable preservatives, such as sodium benzoate, may be also added where indicated.

The present drug delivery device comprises the drug-containing diffusion matrix which can be applied as a transdermal patch with means for fastening the matrix to the skin of a patient. Such means can take various forms, such as an occlusive backing layer forming a kind of "bandage" with the diffusion matrix being held against the skin of a patient being treated. A polyethylene or Mylar tape is contemplated as one form of occlusive layer in accordance with the present invention. It can also take the form of an elastic band, such as a cloth band, a rubbery band, or other material. Here, the diffusion matrix is placed directly on the skin and held in place over the arm or wrist of the patient. An intermediate adhesive layer between the diffusion matrix and the skin capable of permitting the transdermal application of the drug can also be used.

In a further aspect of the present invention, there is substituted for the polyvinylalcohol component a mixture of the same relatively high molecular weight polyvinylalcohol component and a portion of lower molecular weight polyvinylalcohol. The higher molecular weight polyvinylalcohol component is present in the final composition in an amount of from about 5 to about 20% by weight, and preferably about 10% by weight. The lower molecular weight component has a molecular weight of from about 10 to about 25% by weight, and preferably about 15% by weight. The molecular weight ranges from about 4,000 to about 15,000, with 10,000 being a preferred embodiment. The degree of hydrolysis of this lower molecular weight portion is preferably at least about 75%, and preferably about 88%. Optionally included in this second aspect of the present invention is a solubilizing agent which functions to bring the components into solution, which is present preferably in an amount of from about 5 to about 20% by weight, diethanolmyristoylamide being a preferred embodiment.

The invention is illustrated by the following non-limiting examples:

EXAMPLE I

Together there are mixed 20 gm glycerol and 55 ml water. This mixture is heated to 90° C.; after reaching at least 70° C., there are slowly added 15 gm polyvinylalcohol (PVA 100% hydrolyzed, molecular weight 115,000) and 8 gm polyvinylpyrrolidone (mw 40,000). The mixture is stirred at 90° C. until solution is effected, which may take about 10 minutes; it will be appreciated that with larger quantities, a considerably longer period of time may be needed. 98 ml of this solution is then mixed with 2 gm propranolol, this mixture then being mechanically stirred until homogeneous. The homogeneous mixture is then poured into forms made of glass or stainless steel which serve as templates to produce a diffusion matrix having a thickness of about 0.2 to 2 mm. This diffusion matrix is then cut into square pieces of about 1 inch on each side, i.e., to provide a total surface area of about 6.5 cm².

The diffusion matrix is applied to the skin of a patient in need of a beta-blocking effect, the propranolol being transdermally delivered. The diffusion matrix is ideally applied to the skin of the patient by means of a single-piece bandage having the diffusion matrix in the center under the occlusive layer, the bandage being provided to the patient with a peel-off cover much like a "band-aid".

EXAMPLE II

In place of the glycerol of Example I, there is substituted 10 gm polyethyleneglycol having a molecular weight of 1000 and 10 ml water. The resultant diffusion matrix is more rigid than that of Example I.

EXAMPLE III

In place of the polyvinylalcohol and polyvinylpyrrolidone of Example I, there are substituted 2 gm agarose and 21 ml water, yielding a diffusion matrix for the delivery of propranolol.

EXAMPLE IV

The following mixture, listed in parts by weight, is heated under pressure, about 3 atmospheres being suitable, to 110°–130° C.:

| | | |
|---|---|---|
| Polyvinylalcohol | 20 parts | (115,000 mw) |
| Polyvinylpyrrolidone | 15 parts | (40,000 mw) |
| Polyethyleneglycol | 5 parts | (4,000 mw) |
| Glycerol | 3 parts | |
| Propranolol | 2 parts | |
| Water | to 100 parts | |

This mixture is first prepared by heating polyvinylalcohol and water to effect dissolution. The polyethyleneglycol (4,000 mw), polyvinylpyrrolidone, and glycerol are dissolved in cold water, and the two aqueous mixtures are brought together under heat and pressure as described above. Finely divided propranolol is rapidly mixed into the viscous liquid and the mixture is extruded into an appropriate mold.

EXAMPLE V

In place of polyethyleneglycol (4,000 mw) of Example IV, polyethyleneglycol (1,000 mw) is used in the mixture.

EXAMPLE VI

In a further aspect, there is provided an improvement wherein there is included about 10% by weight diethanolmyristoylamide, in the procedure of Example I.

EXAMPLE VII

In a further aspect, there is provided an improvement wherein there is included about 10% by weight diethanolmyristoylamide and the 15 gm polyvinylalcohol of Example I is replaced by 8 gm polyvinylalcohol having a molecular weight of 115,000 (100% hydrolyzed) and 7 gm polyvinylalcohol having a molecular weight of 10,000 (88% hydrolyzed), in the procedure of Example I.

What is claimed is:

1. A self-supporting polymeric diffusion matrix for the sustained release of propranolol in order to deliver said propranolol to a patient, said matrix comprising from about 1 to about 60% by weight of a polar plasticizer, from about 5 to about 20% by weight polyvinylalcohol having a molecular weight from about 50,000 to about 150,000, from about 10 to about 25% by weight polyvinylalcohol having a molecular weight from about 4,000 to about 15,000, from about 2 to about 30% by weight polyvinylpyrrolidone, a pharmaceutically effective amount of the propranolol to provide a sustained release of said propranolol over a prolonged period, and from about 5 to about 20% by weight of diethanol myristoylamide, effectively functioning to bring the components into solution, said matrix having been formed from said solution.

* * * * *